US005474755A

United States Patent [19]
Hanna, Jr. et al.

[11] Patent Number: 5,474,755
[45] Date of Patent: *Dec. 12, 1995

[54] TUMOR ASSOCIATED MONOCLONAL ANTIBODIES

[75] Inventors: Michael G. Hanna, Jr., Frederick; Martin V. Haspel, Seneca, both of Md.; Herbert C. Hoover, Jr., Hingham, Mass.; Marie E. Dembinsky, Frederick; Barry J. Kobrin, Silver Spring, both of Md.

[73] Assignee: Akzo Nobel N.V., Arnhem, Netherlands

[*] Notice: The term of this patent shall not extend beyond the expiration date of Pat. No. 5,106,738.

[21] Appl. No.: 449,613

[22] Filed: May 24, 1995

Related U.S. Application Data

[63] Continuation of Ser. No. 192,089, Feb. 2, 1994, abandoned, which is a continuation-in-part of Ser. No. 65,517, May 21, 1993, abandoned, which is a continuation of Ser. No. 636,179, Dec. 31, 1990, abandoned, which is a continuation-in-part of Ser. No. 302,155, Jan. 25, 1989, Pat. No. 5,106,738, which is a continuation-in-part of Ser. No. 697,078, Jan. 31, 1985, Pat. No. 4,828,991, which is a continuation-in-part of Ser. No. 575,533, Jan. 31, 1984, abandoned.

[51] Int. Cl.$^6$ .......................... A61K 49/00; G01N 33/58; C12N 5/22; C07K 16/30
[52] U.S. Cl. ...................... 424/1.49; 424/9.1; 435/240.2; 435/240.27; 435/7.23; 435/7.9; 530/387.1; 530/387.3; 530/388.3; 530/391.3
[58] Field of Search ................................ 424/1.49, 9.1; 435/240.2, 240.27, 7.23, 7.9; 530/387.1, 387.3, 388.8, 391.3

[56] References Cited

U.S. PATENT DOCUMENTS

| | | |
|---|---|---|
| 4,172,124 | 10/1979 | Koprowski et al. . |
| 4,196,265 | 4/1980 | Koprowski et al. . |
| 4,340,586 | 7/1982 | Bekierkunst et al. . |
| 4,471,057 | 9/1984 | Koprowski et al. . |
| 4,522,918 | 6/1985 | Schlom . |
| 4,612,282 | 9/1986 | Schlom et al. . |
| 4,613,576 | 9/1986 | Cote et al. . |
| 4,618,577 | 10/1986 | Handley et al. . |
| 4,661,586 | 4/1987 | Levy et al. . |
| 4,828,991 | 5/1989 | Hanna et al. . |
| 4,997,762 | 3/1991 | Hanna et al. . |

FOREIGN PATENT DOCUMENTS

| | | |
|---|---|---|
| 793000415 | 1/1978 | European Pat. Off. . |
| 0488470 | 11/1991 | European Pat. Off. . |

OTHER PUBLICATIONS

DeJager et al., "Current Status of Cancer Immunodetection with Radiolabelled Human Monoclonal Antibodies," *Seminars in Nuclear Medicine*, vol. XXIII, No. 2 (Apr.), 1993, pp. 165–179.
G. Winter et al., "Antibody–based Therapy", *TIPS*, pp. 139–143.
Murray et al., "Tissue Reactivity of a Human IgG Monoclonal Antibody Derived from a Patient Immunized with Autologous Colon Carcinoma Cells," *Proceedings of the American Association for Cancer Research*, p. 261, column 2, Abstract No. 1553, Mar. 1991.
Teng, N. N. H. et al., PNAS, 80:7308–7312, Dec. 1983.
Serafini, A. N. et al., J. Nucl Med, 34(5 Supple): Abst #1007, p. 214P, Jun. 8, 1993. (Abst).
Eardi, Y. E. et al., Cancer, 73(3 Supp): 923–931, Feb. 1, 1994 (Meeting Held Sep. 17–19, 1992.
Subramanian, R. et al., Proc Am Assoc Cancer Res Anna Meet, 32: 244, 1991. (Abst).
Jean L. Marx, "Monoclonal Antibodies in Cancer," *Science*, vol. 216 (1982), pp. 283–285.
R. K. Oldman and R. V. Smalley, "Immunotherapy: The Old and the New," *J. Biol. Response Modifiers*, vol. 2 (1983), pp. 1–37.
Paul T. Stratte et al., "In Vivo Effects of Murine Monoclonal Anti–Human T Cell Antibodies in Subhuman Primates," *J. Biol. Response Modifiers*, vol. 1 (1982), pp. 137–148.
R. J. Cote et al., "Generation of Human Monoclonal Antibodies Reactive with Cellular Antigens," Proc. Natl. Acad. Sci., vol. 80 (Apr. 1983), pp. 2026–2030.
H. C. Hoover, Jr. et al., "Delayed Cutaneous Hypersensitivity to Autologous Tumor Cells in Colorectal Cancer Patients Immunized with an Autologous Tumor Cell: Bacillus Calmette–Guerin Vaccine," *Cancer Research*, vol. 44 (Apr. 1984), pp. 1671–1676.
L. C. Peters et al., "Preparation of Immunotherapeutic Autologous Tumor Cell Vaccines from Solid Tumors," *Cancer Research*, vol. 39 (Apr. 1979), pp. 1353–1360.
L. Lindholm et al., "Monoclonal Antibodies against Gastrointestinal Tumour–Associated Antigens Isolated as Monosialogangliosides," *Int. Arch. Allergy Appl. Immuno.*, vol. 71 (1983), pp. 178–181.
H. Koprowski et al., *Somat. Cell Genet.*, vol. 5 (1979), pp. 957–972.
L. Ollson and H. S. Kaplan, "Human–human Hybridomas Producing Monoclonal Antibodies of Predefined Antigenic Specificity," Proc. Natl. Acad. Sci., vol. 77, pp. 5429–5431.
J. L. Butler et al., "Delineation of Optimal Conditions for Producing Mouse–Human Heterohybridomas from Human Peripheral Blood B Cells of Immunized Subjects," *J. Immunology*, vol. 130, No. 1, pp. 165–168.
*Frederick Cancer Research Center Annual Report*, 1980, "Immunotherapy," pp. 64–65.
R. Levy et al., *Annual Review of Medicine*, vol. 34, pp. 107–116 (1983).
M. Herlyn et al., *Proc. Natl. Acad. Sci., USA*, vol. 76(3), pp. 1438–1442 (Mar., 1979).
M. Herlyn et al., *J. Clinical Immunology*, vol. 2(2), pp. 135–140 (1982).

(List continued on next page.)

Primary Examiner—Margaret Parr
Assistant Examiner—Susan A. Loring
Attorney, Agent, or Firm—Mary E. Gormley; William M. Blackstone

[57] ABSTRACT

This invention relates to monoclonal antibody 88BV59 produced by B-cell lines derived from B-cells of cancer patients actively immunized with autologous tumor antigen. These monoclonal antibodies can be used in both diagnostic procedures and therapy for human cancers.

11 Claims, No Drawings

OTHER PUBLICATIONS

M. Herlyn et al., *Int. J. Cancer*, vol. 27, pp. 769–774 (1981).

Z. Steplewski et al., *Cancer Research*, vol. 41, pp. 2723–2727 (Jul., 1981).

*Stedman's Medical Dictionary*, 24th Ed., Williams & Wilkins, Baltimore, Md., (1982), p. 144.

*Handbook of Monoclonal Antibodies*, A. Ferrone et al., Eds. Noyes Pub. (1985), pp. 304–346.

*Monoclonal Antibodies in Clinical Medicine*, A. J. McMichael et al., Ed., Academic Press, London (1982), pp. 111–128, E. S. Lennox et al.

*Monoclonal Antibodies in Clinical Medicine, Mc Michael et al., Ed.*, A. J. (1982), pp. 17–35, Kaplan et al. Academic Press London.

*Monoclonal Antibodies and Cancer*, B. D. Boss et al., Eds., Academic Press, Orlando (1983), pp. 135–142, N. N. H. Teng et al.

*Monoclonal Antibodies and Cancer*, B. D. Boss et al., Eds., Academic Press, Orlando (1983), pp. 143–155, K. A. Foon et al.

*Monoclonal Antibodies and Cancer*, B. D. Boss et al., Eds., Academic Press, Orlando (1983), pp. 163–170, M. C. Glassy et al.

*Monoclonal Antibodies and Cancer*, B. D. Boss et al., Eds., Academic Press, Orlando (1983), pp. 171–180, K. Sikora et al.

*Monoclonal Antibodies and Cancer*, B. D. Boss et al., Eds., Academic Press, Orlando (1983), pp. 181–184, P. A. W. Edwards et al.

D. Kozbor et al., *Proc. Natl. Acad. Sci*, vol. 79, pp. 6651–6655 (1982).

T. Takayama, *Nihon. Univ. J. Med.*, vol. 26, No. 5, Abstract, (1984).

J. E. Boyd et al., *Trends in Biotechnology*, vol. 2, No. 3, pp. 70–77, (1984).

D. L. Toffaletti et al., *J. of Immunology*, vol. 130, No. 6, pp. 2982–2986 (1983).

R. W. O'Donnell et al., *Som. Cell Mol. Gen.*, vol. 10, No. 2, pp. 195–204 (1984).

Haspel et al., *Cancer Research*, vol. 45, pp. 3951–3961 (Aug. 1985).

Finan et al., *Br. J. Cancer*, vol. 46, No. 1, Abstract (1982).

Sikora et al., *Br. J. Cancer*, vol. 43, No. 5, pp. 696–700.

Sikora et al., *Nature*, vol. 300, pp. 316–317.

Wunderlich et al., *Eur. J. Cancer Clin. Oncol.*, vol. 17, No. 7, pp. 719–730.

J. Schlom et al., *Prac. Natl. Acad. Sci., USA*, vol. 77, No. 11, pp. 6841–6845, (Nov., 1980).

Kohler et al., *Nature*, vol. 256, pp. 495–498 (Aug. 1975).

Liao et al., *Cancer Research*, vol. 38, No. 12, pp. 4395–4400 (1978).

E. D. Sevier et al., "Monoclonal Antibodies in Clinical Immunology," *Clin. Chem.*, vol. 27, No. 11, pp. 1797–1806, 1981.

TUMOR ASSOCIATED MONOCLONAL ANTIBODIES

This is a continuation of U.S. Ser. No. 08/192,089, filed Feb. 2, 1994, now abandoned, which is a continuation-in-part of U.S. Ser. No. 08/065,517, filed May 21, 1993, abandoned, which is a continuation of U.S. Ser. No. 07/636,179, filed Dec. 31, 1990, abandoned, which is a continuation-in-part of U.S. Ser. No. 07/302,155, filed Jan. 25, 1989, now U.S. Pat. No. 5,106,738, which is a continuation-in-part of U.S. Ser. No. 06/697,078, filed Jan. 31, 1985, now U.S. Pat. No. 4,828,991, which is a continuation-in-part of U.S. Ser. No. 06/575,533, filed Jan. 31, 1984, now abandoned.

FIELD OF THE INVENTION

This invention relates to monoclonal antibodies produced by hybridoma or transformed B-cell lines derived from B-cells of cancer patients actively immunized with autologous tumor antigen. These monoclonal antibodies can be used in both diagnostic procedures and therapy for human cancers. This invention also relates to cell lines producing these monoclonal antibodies, and to diagnostic procedures and therapeutic approaches using them.

BACKGROUND OF THE INVENTION

This invention relates to new human monoclonal antibodies that react specifically with antigens associated with particular cancers and to hybridoma and transformed B-cell lines for their production derived from peripheral blood B-cells of actively immunized patients. This invention also relates to diagnostic procedures and cancer therapy using these monoclonal antibodies.

Currently available treatments for cancer, particularly radiation therapy and chemotherapy, are based upon the rationale that cancer cells are relatively more sensitive to these treatments than normal cells. However, severe toxicity for normal tissues imposes major limitations to these therapies. In contrast, antibody molecules exhibit exquisite specificity for their antigens. Researchers have therefore sought to isolate antibodies specific for cancer cells as the "long-sought 'magic bullet' for cancer therapy" Jean L. Marx, *Science*, Vol. 216, 283–285 (1982).

Antibodies are protein molecules normally synthesized by the B-cell lymphocytes produced by bone marrow and carried in the blood stream. For any antigen entering the body, i.e., any foreign molecule from a simple organic chemical to a complex protein, antibodies are produced which recognize and attach to that particular chemical structure. The unique chemical structure on the antigen to which a particular antibody can bind is referred to as an antigenic determinant or epitope. B-cell lymphocytes in the body, referred to as B-cells, lymphocytes, or leukocytes, exist as hundreds of millions of different genetically programmed cells, each producing an antibody specific for a different determinant. An antigen, which stimulates antibody production, can have several determinants on its surface. On encountering an antigen, a B-cell carrying on its surface an antibody specific for a determinant on that antigen will replicate. This clonal expansion results in many daughter cells that secrete that antibody into the blood stream.

Because of the specificity of antibodies in recognizing and binding to antigens, it was desired to produce antibodies in quantity that are specific for a single determinant, thus binding only to antigens or tissues having that particular determinant.

B-cells do not grow in a continuous culture unless they have been altered by hybridization with an "immortal" cell or by being transformed with either viral or tumor DNA. Kohler and Milstein (*Nature,* 1975, 256:495) demonstrated that hybrid cells could be prepared by somatic cell fusion between lymphocytes and myeloma cells that grow in culture and produce antibodies specific for a single determinant. These hybrids are referred to as "hybridoma cells." Hybridoma cells are prepared by fusing lymphocytes that have been activated to produce a particular antibody with myeloma cells. When cultured, hybridomas produce antibodies specific for a single determinant on a particular antigen. Such antibodies are referred to as "monoclonal antibodies."

Monoclonal antibodies may also be produced by B-lymphocyte cell lines that have been transformed, either spontaneously or intentionally, with a lymphotropic virus such as Epstein-Barr Virus (EBV). Transformation can also be accomplished using other transforming agents, such as viral DNA and cellular DNA. These cells, unlike hybridoma cells, possess a normal human diploid number (46) of chromosomes. This invention permits the isolation of both hybridomas and transformed B-cell lines that produce monoclonal antibodies. For sake of simplicity, both cell types will be referred to as monoclonal antibody producing cells below.

Monoclonal antibodies are synthesized in pure form uncontaminated by other immunoglobulins. With monoclonal antibody producing cells it is possible to produce virtually unlimited quantities of an antibody that is specific for one determinant on a particular antigen.

It has been believed that if antibodies specific for particular cancer cells were available, they could be used in various methods of treatment and diagnosis. Such antibodies could inactivate or kill particular tumor cells merely by attaching to the cell at the determinant for which they are specific. Alternatively, these antibodies may bind to the surface of effector lymphocytes or macrophages, converting them into tumor antigen-specific killer cells.

Monoclonal antibodies can also increase the specificity of chemotherapeutic drugs, toxins and radioactive isotopes, thus increasing their efficacy while decreasing their toxicity by being conjugated to them. In addition, antibodies conjugated with radionuclides or metallic tracers can be used for imaging for in vivo diagnosis and localization of metastases, such as with proton emission (PET), nuclear magnetic resonance (NMR), computed tomography (CT), and planar and single photon emission computed tomography. The antibodies can also be used for detecting the presence of tumor antigens in blood, as a diagnostic and/or prognostic test for cancer. Also, monoclonal antibodies can be used to isolate tumor antigens for potential use in a standardized vaccine.

The existence of antigens associated with animal tumors was documented in the last century, and the antigenic character of human cancers has been well established, primarily through recent studies with monoclonal antibodies. However, until the research which resulted in this invention, few cancer antigens have actually been characterized in molecular terms and only one group of antigenic determinants associated with human cancers, immunoglobulin idiotypes of B-cell tumors, has been described as being uniquely tumor-specific, i.e., occurring with a high frequency on tumor cells and not occurring to any significant degree on normal tissues R. K. Oldman and R. V. Smalley, *J. Biol. Response Modifiers,* Vol. 2, pages 1–37 (1983);

Stratte et al., *J. Biol. Response Modifiers*, Vol. 1, pages 137–148 (1982).

Past attempts at deriving monoclonal antibodies specific for human cancers have taken two routes with respect to B-cells: 1) B-cells have been extracted from spleens of mice that were immunized against human tumors, U.S. Pat. No. 4,172,124; and 2) human B-cells have been extracted from either peripheral blood or from lymph nodes draining tumors in cancer patients. Neither approach has yielded satisfactory results.

Mice immunized against human tumors have too broad a reactivity. That is, most of the mouse monoclonal antibodies generated react with human antigens present on normal as well as on tumor tissue. An antibody that reacts only with tumor cells is very difficult to select from among the large variety of antibodies produced. For example, 20,000 hybridomas derived from mice immunized with human small-cell lung carcinoma were screened for reactivity with tumor cells Jean L. Marx, *Science*, Vol. 216, 283–285 (1982). In contrast to a very low frequency (<0.4%) observed by this research group, the present invention results in up to 16% of the hybridomas derived from immunized colon patients producing monoclonal antibodies that react specifically with tumor cells. In addition, monoclonal antibodies derived from mouse B-cells have limited potential for application in cancer therapy. After repeated administration they stimulate the human immune system to produce "anti-mouse" antibodies which, in clinical trials, have been shown to neutralize the activity of mouse monoclonal antibodies. The use of our human monoclonal antibodies can circumvent these difficulties.

Another apparent difference between human and mouse monoclonal antibodies is their patterns of labeling. Previous studies with mouse antibodies have demonstrated that there is often a heterogenous labeling of cells within tumor sections. This pattern of reactivity has been attributed by some authors to antigenic heterogeneity of tumor cells (Hand et al., *Cancer Research*, 43:728–735, 1983). In contrast, the human monoclonal antibodies developed by our strategy were homogeneous in terms of their reactivity with tumors to which they did react. A plausible explanation for the heterogenous staining of mouse monoclonal antibodies is that it is a reflection of the murine immune recognition of phase- or cell-cycle-specific differentiation antigens abundant on the tumor cells rather than putative tumor associated antigens. It is not unreasonable to expect that when one immunizes mice with human tumor cells there would be substantial antigenic competition resulting in the more abundant and more predominant tissue-type and differentiation antigens successfully competing with relatively minor tumor associated antigens for immune responsiveness by the host. Thus, autologous immunization of man may result in the elicitation of antibodies against the group of antigens normally poorly immunogenic in mice. This evidence suggests that humans and mice may respond to different tumor antigens. In concert with this hypothesis is our finding that none of the first 36 human monoclonal antibodies we produced appeared to react with carcinoembryonic antigen (CEA), an antigen frequently recognized by murine monoclonal antibodies made against human tumor cells.

The majority of past attempts to develop human monoclonal antibodies have used B-cells extracted from either peripheral blood or lymph nodes from patients bearing tumors. It was believed that the presence of the antigenic tumor would cause a tumor-bearing individual to mount an immune response against his tumor and produce specifically immune B-cells. Thus, B-cells were taken from lymph nodes draining tumors in cancer patients or from circulating lymphocytes found in peripheral blood. However, prior to the present invention, there has been limited success in creating tumor-specific monoclonal antibodies.

The major problem in creating monoclonal antibodies specific for human tumor antigens has been the inability to find a source of specifically immune B-cells Jean L. Marx, *Science*, Vol. 216, 283–285 (1982). In humans, the initial foci of cancer cells tend to grow over long periods of time, from 1% to 10% of the human lifespan, before there is any palpable clinical evidence of the disease. By this time patients are immunologically hyporesponsive to their tumors, or possibly immunologically tolerant. Thus, prior to the present invention, human monoclonal antibodies reactive with tumor cells could not reproducibly be obtained. Furthermore, of the small number of human monoclonal antibodies obtained from cancer patients, very few reacted with determinants found on the surface of tumor cells, but rather with intracellular determinants (R. J. Cote et al, *PNAS*, 1983, 80:2026). The present invention permits the development of monoclonal antibodies reactive with surface antigens, a requisite activity for tumor imaging and therapy.

SUMMARY OF THE INVENTION

One object of the present invention was to develop monoclonal antibodies specifically reactive with tumor-associated antigens that induce an immune response in patients having particular cancers. Such antibodies provide a means for detecting and diagnosing tumors. A second objective of this invention was to obtain monoclonal antibodies that are effective for treating patients with particular types of cancer.

We have developed a new and more effective approach for obtaining monoclonal antibodies by using peripheral blood B-cells from patients immunized with cells from their own tumors in specific vaccine preparations. To achieve active specific immunotherapy, patients were immunized with autochthonous tumor cells, that is, cells from their own tumors. This approach was taken based on our theory that tumor cells express tumor-specific antigens.

Humans mounting an objective immune response against tumor cells were specifically found to be a good source of activated B-cells. We have shown that the peripheral blood of patients who had been actively immunized against their own tumors is an abundant source of such activated B-cells.

We demonstrated in clinical studies that an objective immune response is generated on treating patients having the particular cancer by skin testing, i.e., delayed cutaneous hypersensitivity (DCH). Immunized patients showed delayed cutaneous hypersensitivity to their own colorectal cancers. In addition, the monoclonal antibodies developed from the immunized patient's B-cells reacted with tumors of the same histological type in other patients. These results indicate that the patient's humoral immune response, production of antibodies, is directed against colorectal cancer generally and is not unique to the immunized patient's own tumor. This general response is especially important for the development of a standardized vaccine.

The generation of B-cells that produce antibodies having reactivity specific for epitopes on tumor cell associated antigens, particularly cell surface antigens as in the majority of cases, is an advantageous result that was speculative, at best, when the immunization studies were begun. Only the immunization treatment was observed and measured during the animal studies on which the human immunization procedures were based, not the production of tumor specific antibodies.

The general immune response accompanied by an improvement in the subject's condition was indicative of a cellular response in which macrophages and T-cells become activated in the presence of tumor cell antigens and destroy the tumor cells. Although an antibody response would predictably be triggered by immunization under most circumstances, the time course of the antibody response and the cellular response would in most instances be different. Moreover, the fact that the patients were being immunized with autologous tumor cells, i.e., the patient's own tumor cells, and the experience of previous investigators that little or no antibody production is triggered by a patient's own tumor, made our discovery that B-cells that produce tumor specific antibodies are generated after immunization an unexpected beneficial result.

Some cellular and humoral immune responses can occur independently of each other. For example, it is possible to mount a humoral response in the absence of demonstrable cellular immunity. Conversely, potent cellular immunity, particularly delayed cutaneous hypersensitivity (DCH), may develop despite a minimal antibody response. It was surprising, therefore, for the subjects who showed a positive response to active immunotherapy to have been excellent sources of B-cells producing tumor specific antibodies, particularly cell surface antibodies.

This invention comprises the preparation of successful vaccines for active specific immunization, procedures for extracting immunized B-cells, the production of monoclonal antibody producing cell lines and the production of monoclonal antibodies. Malignant tumors are digested using enzyme preparations. The cells obtained are treated to yield a non-tumorigenic tumor cell preparation having the requisite cell viability, which is injected as a vaccine into the subject from which the tumor was obtained. Peripheral blood B-cells are obtained from the inoculated subject after a predetermined interval and are used to prepare monoclonal antibody producing cells by fusing with myeloma cells, after which the fused cells are screened for the synthesis of immunoglobulin. Monoclonal antibody producing cells may also be obtained by selecting spontaneously transformed B-cells that are able to survive in continuous culture, or by exposing B-cells to an agent capable of transforming cells such as Epstein Barr Virus (EBV) or another lymphotropic virus.

Larger amounts of antibodies may be obtained by fusing EBV-transformed cells with mouse myeloma cells or human-mouse heteromyelomas. Cells that synthesize immunoglobulin are tested for production of antibodies that react with antigens characteristic of the malignant tissue. Those selected are cultured to produce monoclonal antibodies that react with the particular type of tumor with which the subject was afflicted.

This invention also comprises the immunodetection of cancer with labeled monoclonal antibodies. That is, the monoclonal antibodies can be used as radioimmunoscintography (RIS) agents for diagnostic purposes.

DETAILED DESCRIPTION OF THE INVENTION

This invention comprises, specifically, a human diploid cell line, an immortalized human B-cell line that we transformed by exposure to EBV, designated CO88BV59, and subclones and derivatives thereof. One particular derivative of this EBV transformed B-cell line, which has desirable characteristics such as high production of antibody, is the cell line designated CO88BV59H21-2V67-66. This cell line was obtained by first incubating the CO88BV59 cell line with a human-mouse heteromyeloma under conditions suitable for cell fusion to produce a cell line designated CO88BV59H21-2. CO88BV59H21-2 was then exposed to EBV under conditions suitable for transformation to produce CO88BV59H21-2V67-66. All clones and derivative cell lines of CO88BV59 studied so far produce a human $IgG_3$ kappa light chain antibody specifically reactive with an epitope on a cytoplasmic antigen defined in co-owned U.S. Pat. No. 5,338,832 issued Aug. 16, 1994 and referred to as "CTA-1" or as the 16.88 antigen. This antigen was first identified using human IgM antibody 16-88, defined in our copending application Ser. No. 07/038,811, filed Apr. 15, 1987, now U.S. Pat. No. 4,997,762. Hereinafter, the $IgG_3$ antibody produced by all of these "88BV59" cell lines will be referred to as the "88BV59" antibody. Both the 88BV59 antibody and the 16-88 antibody recognize the same tumor associated antigen, but react with different epitopes on that antigen. The present invention includes not only the antibodies produced by the aforementioned cell lines, but an antibody produced by any cell line that functions in the same way as the 88BV59 antibody; in order words, any antibody that binds to the same epitope on the same antigen as the 88BV59 antibody. Finally, the term "antibody" is intended to include any functional fragments of the 88BV59 antibody, such as fragments containing the variable region(s) (heavy and/or light chain) and portions containing complimentary determining region(s). Such fragments may be produced recombinantly by methods known in the art. An example of a recombinantly produced antibody is one in which the $CH_2$ region is deleted ($\Delta CH_2$). Methods are known in the art for making a $\Delta CH_2$ antibody, and it is believed that modifying the antibody in this manner will allow for better in vivo clearance inter alia. Such an antibody, insofar as it is a fragment of the original antibody, is intended to be covered by the present invention. The variable region(s) have been sequenced and are disclosed in copending U.S. Ser. No. 07/807,300, filed Dec. 13, 1991, which is incorporated herein by reference.

The key aspects of this invention are:

1) Criteria for successful vaccines for active specific immunization:

Tumor cells, whole cells enzymatically dissociated from tissue, cryopreserved and X-irradiated for non-tumorigenicity.

Adjuvant, an immunomodulator that is capable of inducing immunogenicity to the tumor cell preparation.

Components and administration, including ratio of adjuvant to tumor cells, optimum doses of tumor cells, and regimen of vaccination.

Patient, regional lymph nodes draining the vaccination site must be present during the first 21 days after vaccination.

2) Procedures and timing for the extraction of immunized B-cells from the patients.

3) Procedures for the production of hybridomas or transformation of lymphocytes and the production of monoclonal antibodies.

4) Procedures for the use of the monoclonal antibodies in diagnosis and therapy of cancer.

We have successfully digested solid human malignancies using various enzyme preparations. The tumor dissociations were evaluated for yield of tumor cells per gram of tissue, cell types recovered, cell viability, cell size, and sterility. The criteria for successful vaccines for active specific immunotherapy are shown in Table 1.

Tumor tissue was obtained from patients suffering from the particular solid cancer for which monoclonal antibodies were to be prepared. The tumor tissue was surgically removed from the patient, separated from any non-tumor tissue, and cut into small pieces. We found it satisfactory to cut the tumor tissue into fragments 2–3 mm in diameter. The tumor fragments were then digested to free individual tumor cells by incubation in an enzyme solution.

After digestion, the freed cells were pooled and counted, and cell viability was assessed. The trypan blue exclusion test was found to be an acceptable measure of cell viability. The tumor cells were then cryopreserved and stored in liquid nitrogen.

The vaccine was prepared for injection by rapidly thawing cryopreserved cells, diluting the cells, washing with HBSS, resuspending, counting, and assessing viability.

Viable tumor cells were irradiated to render them non-tumorigenic. We found that irradiation with 4020 rads/min for a total of 20,000 rads resulted in non-tumorigenic but viable cells. The volume of the cell suspension in HBSS was adjusted such that $10^7$ viable cells remained in the tube. The cells were centrifuged, the supernatant was removed, and $10^7$ viable BCG were added in a volume of 0.1 ml. Hank's Balanced Salt Solution (HBSS) was added in sufficient quantity for a final volume of 0.2 ml. A third vaccine was similarly prepared, omitting the BCG.

Immunization of Patients

Patients afflicted with the particular solid cancer for which antibodies were to be generated were immunized by intradermal inoculation with the tumor cell vaccine. $10^7$ viable tumor cells admixed with BCG were used for the first two vaccinations and $10^7$ tumor cells alone were used for the third vaccination. Scheduling each vaccination one week apart was found to be a successful procedure for inducing antibody production by the patient's peripheral blood lymphocytes.

Collection of Immunized B-Cells

Venous blood was collected from the immunized patients one week after each vaccination. Peripheral blood lymphocytes (PBLs) were separated from the collected blood for use in hybridoma production or transformation.

Separation of lymphocytes from the blood was accomplished using two different methods. The first comprised dilution with calcium and magnesium-free HBSS, layering on lymphocyte separation medium, centrifuging, and removing cells at the interface. These cells were diluted with HBSS and pelleted. The lymphocytes were then resuspended in serum-free Hepes-buffered Dulbecco's MEM (DMEM), counted, and assayed for viability (GIBCO Biologics, Grand Island, N.Y.).

An alternative method that was used to recover peripheral blood lymphocytes (PBLs) enriched for B-cells comprised the removal of T-lymphocytes by rosetting with 2-aminoethylisothiouronium bromide hydrobromide (AET) treated sheep erythrocytes. Treated erythrocytes were mixed with peripheral blood lymphocytes, pelleted by centrifugation, and the pellet incubated on ice. After resuspension, layering over lymphocyte separation medium (LSM, Litton Bionetics), and centrifugation of the rosetted cells, the T-cell depleted PBLs were collected at the interface, washed, and pelleted. The PBLs enriched for B-cells were then used for hybridoma generation after counting and viability determination.

Preparation of Human Hybridomas for the Production of Anti-Tumor Monoclonal Antibodies Peripheral blood lymphocytes and cultured myeloma cells were mixed together, pelleted, and resuspended in a serum-free medium. Polyethylene glycol (PEG) was added, the cells pelleted and resuspended in HT medium (DMEM containing 20% fetal bovine serum, hypoxanthine and thymidine) and distributed into microtiter wells. Twenty-four hours later, HAT medium (HT medium containing aminopterin) was added to each well, with one-half of the medium being replaced every three days. After maintenance in HAT medium for 14 days, the cells were maintained on HT medium for an additional two weeks, after which the cells were grown on a DMEM medium containing 20% fetal bovine serum.

The hybridomas were pre-screened for the synthesis of human immunoglobulin using the standard enzyme immunoassay. Hybridomas synthesizing human immunoglobulin in sufficient amounts were tested on tissues. Particular tissue samples were incubated with hybridoma supernatant fluids. Supernatants that demonstrated reactivity with particular tumor tissues indicated that hybridoma cells in the wells from which the particular supernatants were drawn produced tumor-specific antibodies. If the same supernatant failed to show a reaction with samples of normal tissue after extensive screenings, the hybridomas in that particular well were considered tumor-specific. These tumor-specific supernatants were further tested against carcinoembryonic antigen (CEA) to be sure of their narrow specificity.

In addition to hybridoma cells that produced tumor-specific antibodies, transformed human B-cells (diploid cells) that produced tumor-specific antibodies were also prepared by these procedures. The transformed B-cells were detected in the same way as tumor-specific antibody-producing hybridomas. Thus, well supernatants that tested positively for reactions with tumor tissue and negatively for reactions with normal tissue and with CEA contained either hybridomas or transformed B-cells. The two types of cells were differentiated by observing that the transformed B-cells contained 46 human chromosomes, whereas the hybridomas contained many more chromosomes, not all of which were of the human type.

It is apparent that spontaneously transformed B-cells had been exposed to a transforming agent, either in vivo or during the procedures after peripheral blood was collected. One of such agents is Epstein Barr Virus (EBV). We have used EBV transformation for producing antibody producing cells that will live in continuous culture. By this method, B-cells are incubated with EBV for a period of time to let the virus be adsorbed, after which the cells are separated from the EBV containing medium, resuspended, and screened in a similar manner to that described above for screening hybridomas.

Use of the Monoclonal Antibodies in Diagnosis and Therapy of Cancer

The 88BV59 antibody is labeled by conventional methods with radioisotopes or metallic tracers typically used in radiological scanning. These isotopes include, but are not limited to, iodine-131, iodine-125, indium-111 and technetium-99m. The specific activity of the radiolabeled antibody is not particularly limited, and about 2 to about 4 mCi/mg. of antibody has been found acceptable. About 15 to about 41 mCi of $^{99m}$TC- 88BV59 has been infused intravenously over a 30 minute period and good imaging resulted, although this amount may be varied depending on such factors as weight of the patient and safety. Other methods of introduction of the radiolabeled antibody into the body may be used, such as through intralymphatic and intraperitoneal administration. The details of immunodetection with radiolabeled 88BV59 antibody may be found in the review article, DeJager et al., "Current Status of Cancer Immunodetection with Radiolabeled Human Monoclonal Antibodies", *Seminars in Nuclear Medicine*, Volume XXIII, No. 2 (April), 1993: pages 165–179, incorporated herein by reference. The administration of radiolabeled 88BV59 has been shown to be safe and well tolerated with few side effects reported. The data collected so far clearly indicate that antibody scanning with $^{99m}$TC-88BV59 using both planar and tomographic techniques is superior to CT scanning for the detection of intraabdominal and pelvic metastases. The combination of the two modalities appears to give optimal detection. The major advantage 88BV59 has over murine antibodies is its lack of immunogenicity, which makes possible repeated administrations.

EXAMPLE I

Preparation of Sensitized B-Cells

A. Patient Selection.

Patients undergoing surgical resection of colon or rectal cancers were selected for a randomized trial of active specific immunotherapy. Randomization was done with stratification according to pathologic stage and tumor was obtained from all patients who met the clinical criteria. Candidates for the study were colorectal cancer patients with no previous history of cancer, who had received no prior chemotherapy or radiation therapy, and who were in suitable medical condition to comply with the outpatient treatment protocol. Patients eligible for the trial were those with tumor extending through the bowel wall (Astler-Coller B2), positive lymph nodes (stages C1, C2) or patients with metastatic disease (stage D). Within these classifications, patients were randomly selected for participation in treatment and non-treatment groups. Randomization cards were computer generated and sequentially drawn from each category postoperatively.

B. Tumor Acquisition.

After surgical resection the bowel specimen was taken immediately to the hospital pathology department and opened under sterile conditions. Tumor tissue was excised, placed in sterile tubes containing Hank's Balanced Salt Solution (HBSS) containing 50 µg gentamicin per ml and carried immediately on ice to the laboratory for processing and freezing.

C. Dissociation of Solid Tumor and Colon Mucosa.

The tissue dissociation procedure of Peters et al (*Cancer Research*, 39:1353–1360, 1979) was employed using sterile techniques throughout under a laminar flow hood. Tumor tissue was rinsed three times in the centrifuge tube with HBSS and gentamicin and transferred to a petri dish on ice. Scalpel dissection removed extraneous tissue and the tumor was minced into pieces approximately 2 to 3 mm in diameter. Tissue fragments were placed in a 75 ml flask with 20–40 ml of 0.14% (200 units/ml) Collagenase Type 1 (Sigma C - 0130) and 0.1% (500 Kunitz units/ml) deoxyribonuclease type 1 (Sigma D - 0876) (DNAase 1, Sigma D-0876) prewarmed to 37° C. Flasks were placed in a 37° C. waterbath with submersible magnetic stirrers at a speed which caused tumbling, but not foaming. After a 30-minute incubation free cells were decanted through three layers of sterile medium-wet nylon mesh (166t: Martin Supply Co., Baltimore, Maryland) into a 50 ml centrifuge tube. The cells were centrifuged at 1200 rpm (250×g) in a refrigerated centrifuge for 10 minutes. The supernatant was poured off and the cells were resuspended in 5–10 ml of DNAase (0.1% in HBSS) and held at 37° C. for 5–10 minutes. The tube was filled with HBSS, washed by centrifugation, resuspended to 15 ml in HBSS and held on ice. The procedure was repeated until sufficient cells were obtained, usually three times for tumor cells. Cells from the different digests were then pooled, counted, and cell viability assessed by the trypan blue exclusion test. The cells were centrifuged for a final wash prior to cryopreservation.

D. Cryopreservation.

Optimal cryopreservation was a primary concern. For vaccine preparation, the dissociated tumor cells were adjusted to 5–8×$10^7$/ml in HBSS and added in equal volume to chilled 2 X freezing medium containing 15% dimethylsulfoxide (DMSO) and 4% human serum albumin (HSA). The final suspension of 2 to 4×$10^7$ cells/ml were placed in 1.2 ml Nunc freezer vials. For DCH cell testing the procedure was the same except that no HSA was used. In both cases, in preparation for freezing, the Nunc vials were transferred on ice to a Cryo-Med model 990 Biological Freezer with a model 700 Controller and a model 500 Temperature Recorder for controlled-rate freezing. Care was taken that the temperature of the individual vials, including the monitor vial, was uniform at the beginning of the freezing process. Vials were cooled at a controlled rate of –1° C./min to a final temperature of –80° C. The vials were transferred in liquid nitrogen to liquid nitrogen storage.

E. Clinical Protocol.

Patients with tumors of the appropriate pathologic stages were randomized to receive either the autologous tumor cell-BCG vaccine or to have no further therapy. The stage D patients all received 5-fluorouracil chemotherapy and all patients with lesions below the peritoneal reflection (rectal cancer) received 5040 rads of pelvic X-irradiation two weeks after immunotherapy was completed. The vaccines were started at 4–5 weeks after tumor resection to allow sufficient time for recovery of immunologic suppression induced by anesthesia and surgery. At 3– 4 weeks after resection both control and treatment patients were skin tested with standard recall antigens as well as graded doses of their autologous tumor cells. Recall antigens used were: Mumps skin test antigen, USP, Eli Lilly, Indianapolis, Ind.; Aplisol, PPD, (Tuberculin Purified Protein Derivative), Parke-Davis, Detroit, Mich.; Trichophyton, diluted 1:30, Center Laboratories, Port Washington, N.Y.; and Candida albicans diluted 1:100, Center Laboratories, Port Washington, N.Y., 0.1 ml of each was placed intradermally on the forearm and examined for erythema and induration at 24 and 48 hours.

Patients selected for treatment protocol received 3 weekly intradermal vaccine injections consisting of $10^7$ irradiated, autologous tumor cells and $10^7$ BCG in the first 2 vaccines with $10^7$ tumor cells alone in the final. Fresh-frozen Tice BCG, was stored at –70° C. (Organon, Inc., West Orange, N.J., previously supplied by University of Illinois Medical Center, Chicago, Ill.). The first vaccine was placed on the left anterior thigh approximately 10 cm below the groin crease, the second in a comparable location on the right thigh and the third in the right deltoid area.

F. Preparation of Vaccine.

On the day of the first and second vaccinations, the vial was rapidly thawed in a 37° C. waterbath, tumor cells were diluted slowly to 15 ml in HBSS, washed once by centrifugation at 1200 rpm and resuspended to 15 ml in HBSS. Cell counts and viability determinations were made using the trypan blue exclusion test. Viability ranged between 70 and 90%, with a mean of 80%. The cells were washed once by centrifugation at 1200 rpm and resuspended to 15 ml in HBSS. The suspension of tumor cells was placed on ice and irradiated at 4020 rads/min for a total of 20,000 rads. The volume of the cell suspension was adjusted such that $10^7$ viable tumor cells remained in the tube ($1.3 \times 10^7$ viable cells are included to allow for cell loss in tubes and syringes, and for the possibility of approximately 20% misidentification of lymphoid cells). The cells were centrifuged, the supernatant removed and $10^7$ BCG were added in a volume of 0.1 ml. HBSS was added in sufficient quantity for a final volume of 0.2 ml. The third vaccine was similarly prepared, omitting the BCG.

The vaccine suspension was drawn up through a 20 gauge needle into a 1.0 ml tuberculin syringe. The 20 gauge needle was replaced with a 27 gauge needle for the intradermal injection, and the syringe was placed on ice for transport to the clinic.

The patients were observed closely after each vaccine for erythema and induration at the site of injections, fever, lymphadenopathy or any adverse reactions. The first two vaccine sites ulcerated after 2–3 weeks but always healed within 10 to 12 weeks.

G. Results of Immunization.
Reactivity to Standard Recall Antigens

All patients were reactive initially to at least one of the standard recall antigens. In the first group two of 29 were reactive to candida, 26 of 29 were reactive to mumps, 16 of 29 were reactive to PPD and 3 of 29 reacted to trichophyton. There was no significant change in reactivity in the follow-up period except that all but two of the immunized patients converted to PPD positivity.

H. Delayed Cutaneous Hypersensitivity (DCH) to Tumor Cells

Four of 24 patients (17%) had a positive DCH to $10^6$ tumor cells prior to the course of immunization. This was not significantly different from the one of 11 patients (9%) testing positive in the non-immunized control group. Of significance ($p<0.1$), all of the initially four positive responders and 12 of the negative responders in the immunization group boosted to greater DCH reactivity following a course of immunotherapy (67% became positive). Seven of these patients have been tested at one year, with three maintaining a positive response. Only three of the 16 objectively immunized patients demonstrated a positive DCH response to $10^5$ tumor cells at 6 weeks, with none showing a response to $10^4$ cells.

EXAMPLE II

Production of Cells Producing Human Monoclonal Antibodies

A. Removal and Processing of Immunized B-Cells from Patients

Patients were bled at the time of the second immunization, one week after the first immunization, and at the time of the third vaccination, one week after the second immunization. Venous blood was collected aseptically in the presence of preservative-free heparin (O'Neill, Jones and Feldman, St. Louis, Mo.) at a final concentration of 17 units/ml. The blood was maintained at room temperature and transported to the laboratory expeditiously, within a few hours of collection.

The blood, diluted 1:2 with calcium and magnesium-free HBSS, was layered (4 ml) over 3 ml of lymphocyte separation medium (LSM, Litton Bionetics) and centrifuged in a 15 ml centrifuge tube for 30 minutes at 400×g. The cells at the interface were removed, diluted with three times their volume of HBSS and pelleted (1000 rpm for 10 minutes). The peripheral blood lymphocytes were resuspended in 10 ml of serum-free Hepes-buffered Dulbecco's MEM (DMEM), counted and viability determined.

An alternative method was also used to recover immunized B-cells. The T-lymphocytes were removed by rosetting with AET-treated sheep erythrocytes. Sheep erythrocytes (in Alsever's solution) were washed three times with balanced salt solution (BSS) and incubated at 37° C. for 20 minutes with four times the packed cell volume with 0.14M AET (Sigma). The treated cells were then washed three times with HBSS and resuspended to a 10% suspension. The treated erythrocytes were layered over LSM, centrifuged at 2500 rpm and the pellet collected. Following three washes with HBSS, the sheep erythrocytes were resuspended to a 10% suspension in undiluted fetal bovine serum and used within two weeks. The PBLs (up to 80 million cells) were mixed with 1 ml of AET-treated sheep erythrocytes and pelleted at 1000 rpm for 10 minutes at 4° C. The pellet was incubated on ice for 45 minutes, gently resuspended with a wide bore pipette and layered over 3 ml LSM. The rosetted cells were centrifuged at 400×g for 40 minutes at room temperature. The T-cell depleted PBLs were collected at the interface, washed with three times the volume HBSS, and pelleted. Following counting and viability determination, the PBLs enriched for B-cells were then used for hybridoma generation.

B. Generation of Human Hybridomas.

Mouse myeloma cells (NS-I) were grown in the presence of 8-azaguanine (20 µg/ml). Three days before fusion, the cells were pelleted and passaged in medium free of 8-azaguanine. The cells were passaged again the day before fusion to maintain them in log phase. The myeloma cells were washed once with serum-free medium, counted, and viability determined. The PBLs and myeloma cells were mixed at a ratio of 3:1 and pelleted together at 1000 rpm for 10 minutes. All supernatant fluid was removed and the cell pellet resuspended in less than 100 µl of serum-free medium. One ml of polyethylene glycol (50% w/v) prewarmed to 37° C. was added dropwise to the cell pellet over the course of one minute with constant agitation of the tube. Twice the previous volume of pre-warmed serum-free medium was added to the cell suspension over the course of one minute until the 50 ml tube was filled. The cells were pelleted at 800 rpm for 15 minutes. The cells were gently resuspended in HT medium (DMEM containing 20% fetal bovine serum, hypoxanthine 13.6 µg/ml and thymidine 3.9 µg/ml) at a concentration of $2.5 \times 10^6$ cells/ml (pre-fusion count) and 100 µl was added to each microtiter well. Twenty-four hours later, 100 µl of HAT medium (HT medium containing 0.18 µg/ml aminopterin) was added to each well. Half of the medium was replaced every three days with fresh HAT medium. After maintenance of HAT medium for 14 days, the cells were maintained on HT medium for an additional two weeks, at which time the cells were grown on a DMEM medium containing 20% fetal bovine serum.

Alternatively, co-cultivation of PBLs with myeloma cells may be used to generate transformed diploid B-cells. PBLs and myeloma cells were mixed (at a ratio of 3:1), pelleted at 800 rpm and selected in HAT medium, as described above.

C. Screening of Hybridomas.

The hybridomas were first quantified and isotyped by a capture enzyme-linked immunoassay (ELISA) for the synthesis of human immunoglobulin (IgA, IgG and IgM). The standard Bio-EnzaBead method was utilized, which is sensitive in the range of 10–300 ng/ml. The hybridoma supernatant fluids were diluted 1:30 with an effective range of 0.3–9 µg/ml. Only hybridomas that synthesized human immunoglobulin at a concentration of greater than or equal to 1 µg/ml were tested by indirect immunoperoxidase on tissues after the isotype of the antibody (IgA, IgG or IgM) was determined.

Polycarbonate-coated metallic beads (Bio-EnzaBead™, Litton Bionetics) were incubated with goat antibodies to human immunoglobulins (IgG+IgA+IgM) overnight at 4° C. and then blocked (30 min at room temperature) with 2.5% BSA to prevent non-specific binding. The beads were then air dried and stored at 4° C. The ELISA for detection of immunoglobulin was performed as follows. Supernatant fluid from a 96-well culture plate was diluted, incubated with the antibody-capture bead for 1 hr at 37° C., washed, and then incubated for 1 hr at 37° C. with peroxidase-labeled affinity-purified goat antibody to human immunoglobulins (IgG+IgA+IgM). The washed beads were then incubated (10 min at room temperature) with 2,2'-Azino-di[3 -ethyl-benzthiazoline-6-sulfonic acid], and the optical density was determined at 405 nm. The immunoglobulin concentrations were interpolated mathematically from the linear portion of a standard curve (30–1000 ng/ml) of human gamma globulin. Supernatant fluids containing >1 µg/ml were then isotyped using this ELISA with peroxidase-labeled goat antibodies to human γ, α, and µ chains. Subsequent quantitative assays used an immunoglobulin standard appropriate for the monoclonal antibody isotype. Mouse immunoglobulins were assayed with Bio-EnzaBeads coated with goat anti-mouse IgG+IgM (H+L) and peroxidase-conjugated goat antimouse IgG+IgM (H+L). In other experiments, supernatant fluids were incubated with the anti-human Ig beads and the peroxidase-conjugated goat antimouse IgG+IgM (H+L).

Cryostat sections of normal and tumor tissue, stored at −30° C., were post-fixed in PLP (0.5% p-formaldehyde, 0.075M L-lysine, 0.01M sodium periodate) for 20 minutes at 4° C. The sections were then washed. Paraffin sections of 10% formalin-fixed tissues were deparaffinized immediately before use. The cryostat and paraffin sections were then incubated at room temperature in 1% bovine serum albumin in PBS containing 0,075M L-lysine for 20 minutes. The sections were incubated overnight at 4° C. with hybridoma supernatant fluids. Following three washes with PBS, the sections were then incubated with the appropriate anti-human peroxidase-labeled reagent for 60 minutes at 37° C., washed and incubated at room temperature for 15 minutes with diaminobenzidine (0.5 mg/ml, Ph 7.6) in PBS containing 0.1% hydrogen peroxide. The sections were washed with PBS, stained with hematoxylin, dehydrated, and mounted with permount.

These methods permitted the widest spectrum of tissue reactive antibodies to be detected (i.e., directed against surface or cytoplasmic antigens).

To isolate broadly reactive antibodies, the supernatant fluids were screened against a panel of tumor sections. Cell lines producing monoclonal antibodies were then cloned by limiting dilution. Twenty-two fusions were performed with peripheral blood lymphocytes obtained from ten patients, and two fusions were done with lymphocytes from patients before immunization. Optimal results were obtained with lymphocytes removed one week after the second immunization. The frequency of immunoglobulin producing clones isolated after the second immunization was almost twice that after the first immunization. Seven of the 36 tissue-positive monoclonal antibodies reacted with cryostat sections but not with paraffin embedded tissues. This finding underscores the need for broad screening procedures. More than two-thirds of the clones produced IgM, most probably a consequence of the source of the lymphocytes (peripheral blood).

D. Identification of Diploid Cells.

One-third of the cell lines had morphology typical of hybridomas and grew as dispersed cells. Karyotypic analysis of six representative hybrids demonstrated that they were human-mouse heterohybridomas. By contrast, the majority of the monoclonal antibody synthesizing cell lines (24 out of 36) were atypical in appearance. These cells were predominantly irregular in shape and grew in large aggregates. These cluster-forming cells were isolated in seven fusions performed with PBLs from seven of ten colon patients. Thus, they appear to be quite common. Six cell lines representing five fusions from four patients, were karyotyped and were found to contain 46 chromosomes. G-banding of the chromosomes confirmed that they were of human origin. Thus, based upon the criterion of cell morphology, it appears that the majority of the monoclonal antibody-synthesizing cell lines are not hybridomas but rather are transformed human B-cells (diploid cells).

No clear differences exist between these cell types in the isotype of secreted immunoglobulin or the type of tissue stained. The amounts of immunoglobulin (1–60 µg/ml) secreted by both cell types were essentially comparable, with most of the human cells producing 5–20 µg/ml. As may be expected, the diploid cells appear to be more stable with regard to immunoglobulin production. These cells were grown in continuous culture for up to 9 months without any indication of a finite life span for antibody production. In fact, increases in antibody production during long-term culture were observed for some diploid lines. The clones which subsequently became non-producers during extensive cell passage had growth properties typical of hybridomas. However, most hybrids had sufficient stability to permit the production of useful quantities of antibody. For example, human-mouse heterohybridoma 7a2 was passaged for more than 20 generations from a recently cloned seed stock at $5 \times 10^6$ cells without a decrease in antibody production. Thus, the cells theoretically could be expanded to $7 \times 1013$ cells. This hybrid produced approximately 30 µg/ml/$10^6$ cells and thus $7 \times 10^{13}$ cells could conceivably produce over 2 kg of antibody.

E. EBV Transformation Procedure

As an alternative to hybridization, peripheral blood B-cells from immunized patients can be intentionally exposed to transforming agents, resulting in continuously growing cell lines that produce monoclonal antibodies. We have used EBV as the transforming agent, although any effective lymphotropic virus or other transforming agent able to transform the B-cells to grow in continuous culture and still produce monoclonal antibodies specific for tumor associated antigens can be used.

By our method, heparinized blood was separated on an LSM gradient and the mononuclear cell fraction was collected at the interface. The mononuclear cell fraction can either be used at this point or cryopreserved for future transformation.

Prior to transformation, in some instances, we depleted the mononuclear cell fraction of macrophages and other cells that might inhibit transformation. Two techniques used were plastic adherence and treatment with the methyl ester of L-leucine. In the plastic adherence technique, the cells were suspended in cell culture medium (RPMI 1640 medium, Gibco, Grand Island, N.Y.) containing 20% fetal bovine serum ($2 \times 10^6$/ml) and incubated overnight in plastic cell culture dishes. Non-adherent cells were removed from the plastic by pipetting, leaving the lymphocytes. Alternatively, the cells were incubated in methyl ester L-leucine (5 mM in serum-free cell culture medium) for 40 minutes at room temperature and then washed.

The lymphocytes, either fresh or cryopreserved, either unfractionated or depleted of some non-B cells, were counted and between 2 and $5 \times 10^6$ cells were pelleted. The pelleted cells were resuspended in 5 ml of freshly harvested Epstein Barr Virus in the form of undiluted B95-8 supernatant fluid harvested from a 4–6 day old culture of B95-8 cells, clarified by centrifugation at 2,000 rpm for 15 minutes at 4° C. and filtered through a 0.8 micron filter to insure that all cells had been removed. The B95-8-cell line was obtained from Dr. G. Tostado, Division of Biologics, FDA. The cells and EBV were incubated at 37° C. for 90 minutes for virus adsorption. During virus adsorption, the cells were agitated periodically.

After virus adsorption the cells were pelleted at room temperature, resuspended in cell culture medium containing 20% fetal bovine serum and counted. The cells were then diluted to about $5 \times 10^4$ cells/ml and approximately 100 µl plated into each well of a 96 well plate. An additional 100 µl of cell culture medium was then added to each well. Alternatively, the cells may be plated into wells containing irradiated feeder cells (such as J774). The mouse macrophage line J774 (ATCC, Rockville, Md.) were irradiated (20,000 rads) and then cryopreserved. The cells were thawed and then plated ($5 \times 10^3$ cells/well) into 96 well plates one day before the EBV transformation were to be seeded.

The cell culture media was changed twice per week for up to 6–8 weeks. Screening of supernatant fluid from wells exhibiting extensive cell growth to select those synthesizing human immunoglobulin and the culturing of selected cell lines was performed according to the procedures described above for selection and culturing of monoclonal antibody producing cells.

F. Production of Monoclonal Antibodies.

Human monoclonal antibody producing cells were grown in RPMI 1640 medium (Gibco, Grand Island, N.Y.) supplemented with 10% fetal bovine serum, 3 Mm L-glutamine and 5 µg/ml gentamicin. The medium was in some cases further supplemented with 25% D-glucose (final concentration 0.25%). The cells were at 37° C. (35°–38° C.) under a humidified atmosphere of 7.5% $CO_2$ in air. The antibody was harvested from the highly metabolized spent medium by pelletizing the medium free of cells (e.g., by centrifuging at 500 rpm for 15 minutes).

EXAMPLE III

Reactivity of Monoclonal Antibodies to Normal and Tumor Tissue

Most of the antibodies exhibited substantially reduced binding to normal colonic mucosa. The antibodies reactive with paraffin sections were also tested for reactivity with normal tissue. 88BV59 showed negative reactivity with the following normal human tissues: ovary, uterus, testes, vagina, adrenal glands, prostate, thyroid, thymus, lymph nodes, spleen, bone marrow, myocardium, cerebral cortical cells, skin, muscle and hemopoietic cells. 88BV59 exhibited slight reactivity with the following tissues: colon (brush border and superficial glands), small intestine (brush border and superficial glands), stomach (gastric pits and superficial glands), esophagus (glands), pancreas (some ductal and exocrine glandular epithelium), kidney (50% of collecting tubules), cervix (epithelial lining (⅔ tissues were positive)), breast (acini and ductal epithelium), lung (some alveolar and bronchial cells), brain (astrocytes (⅔ tissues were positive)), spinal cord (neuropil), skin (50% of glands in dermis) and liver (bile ducts). Reactivity of 88BV59 with human tumor cell lines is shown in Table 2. Table 3 shows the reactivity of 88BV59 with tumor tissue specimens.

EXAMPLE IV

Cancer Immunodetection With Radiolabelled 88BV59 Antibody

Clinical trials have been performed for the detection of cancer with radiolabelled 88BV59 antibody. A Phase I imaging trial consisted of five patients who received 4.0 to 8.8 mg. of 88BV59 antibody labelled with 5 to 13 mCi of $^{99m}$Tc (1.1 to 1.7 mCi/mg.) by IV infusion over 30 minutes; none had a severe adverse reaction. The serum clearance was biphasic with a mean $T_{1/2}$ α of 0.9 hour and $T_{1/2}$ β of 14 hours. Planar and single photon emission computer tomography (SPECT) images were obtained at 4 hours and 20 to 24 hours. More metastatic lesions were observed using radioimmunoscintography (RIS) with SPECT than by using the standard computed tomography (CT) or magnetic resonance imaging (MRI). No human antihuman antibody response was detected in serum.

Sixty-eight patients entered phase II studies; thirty-six of these patients underwent surgery. The data of the surgical patients were used to evaluate the imaging characteristics and to compare the antibody and CT scans in terms of tumor localization. The study was a nonrandomized, single-arm, open-phase II study evaluating the efficacy and safety of $^{99m}$Tc-88BV59 as a RIS agent. Patients were not preselected on the basis of immunohistochemistry or skin test reactivity. They had at least one documented site of tumor involvement by conventional diagnostic techniques or were suspected of recurrent disease on the basis of an elevated CEA. In order to block thyroid uptake and gastric secretion of pertechnetate, fifty-one patients were administered 400 mg. of potassium prochlorate before infusion, 4 hours post infusion, and 24 hours post infusion. Seventeen patients received 88BV59 without potassium prochlorate. Labelling of 88BV59 with $^{99m}$Tc was performed by a direct labelling method using stannous chloride as the reductant. The specificity of $^{99m}$Tc-88BV59 was 2 to 4 mCi/mg. of antibody and the antibody bound $^{99m}$Tc greater than 90%. Following an IV test dose of 300 µg., sixty-eight patients received 15 to 41 mCi of $^{99m}$Tc-88BV59 over a 30 minute period by IV infusion.

The distribution of $^{99m}$Tc-88BV59 in normal organs was assessed at two imaging times: 3 to 4 hours and 16 to 24 hours after antibody administration. At the early imaging time, a vascular blood-pool scan was observed with concentration of the isotope in the heart and great vessels, liver, spleen, kidneys, as well as bladder excretion. At 16 to 24 hours, there was still significant but reduced background activity. The calculated bone marrow dose suggested that there was no targeting of the antibody or accumulation of the $^{99m}$Tc in the bone marrow. Technetium-99m- 88BV59 in doses of less than or equal to 40 mCi may be administered safely for diagnostic purposes.

Technetium-99m-88BV59 using SPECT imaging detected 75% of known abdominal and pelvic lesions. The imaging characteristics of $^{99m}$Tc-88BV59 are best defined in the subset of 36 surgical patients for whom histopathologic validation of imaging is available. The smallest nodule detected was 0.5 cm. in diameter. In the surgical patients, the sensitivity of the antibody scan was greater than the sensitivity of the CT scan: 68% vs. 40% in detecting tumors within the abdomen and pelvis, excluding the liver. The difference is statistically significant (McNemar's test, P>0.05). The antibody scan and CT scan appeared to detect different subsets of tumors within the abdomen. Optimal detection results from the combination of the antibody scan and the CT scan. Together they detect 80% of surgically proven lesions vs. 40% for CT scan alone (McNemar's test, P>0.01). In the case of hepatic metastases an analysis by sight was conducted; the CT scan correctly identified 10 of 13 metastatic livers; the antibody scan, 9 of 13; and the CT and antibody scans combined, 11 of 13. These differences are not statistically significant.

The antibody scan is clearly superior to the CT scan in detecting abdominal and pelvic disease. The antibody scan identifies twice as many lesions as the CT scan. 84% of primary tumors were correctly detected by the antibody scan compared with 37% by CT scan. For recurrent and metastatic tumors, the antibody scan identified 52% of the lesions compared with 43% by CT scan alone. However, antibody and CT scans combined showed a sensitivity of 81%. In order to further evaluate these data, the isotopic dose effect on imaging sensitivity was analyzed. In the analysis of abdominal and pelvic lesions, a dose effect was evident, with the optimal range being 30 to 35 mCi. At the 30 to 35 mCi dose, the sensitivity of the antibody scan was 78%, the specificity 67%, the positive predictive value 82%, the negative predictive value 60%, and the accuracy 74%. These studies are comparable to those of other RIS studies using whole murine or chimeric IgG's.

Techniques including the preparation of protein extracts and the use of immunoadsorbent lectins for the immunization of mice are required to produce monoclonal antibodies against protein antigens derived from colon tumors. Thus, autologous immunization of man elicits antibodies against a group of antigens normally poorly immunogenic for mice. It is therefore possible that man and mice may respond to different tumor-associated antigens. In concert with this hypothesis is the finding that none of 28 different monoclonal antibodies prepared by this method that we examined to-date reacted with purified CEA, an antigen frequently seen by murine monoclonal antibodies made against colon tumor cells, (Koprowski et al, *Somat. Cell Genet.*, 5:957–972, 1979, Morgan et al., *Hybridoma*, 3:3, page 233 (1984).

In addition to providing monoclonal antibodies reactive with tumor cell surface antigens for the in vivo diagnosis and immunotherapy of cancer, the invention provides monoclonal antibodies which will be useful as probes to isolate and characterize the antigens relevant to human cancer immunity. These antigens may ultimately prove useful as a tumor vaccine. In addition, the generation of antibody producing diploid cells adds a dimension of genetic stability to the production of human monoclonal antibodies reactive with tumor cell surface antigens.

The foregoing describes the formation of novel monoclonal antibodies specific for certain tumors, monoclonal antibody producing cell lines, and methods for their preparation. The techniques for preparing the novel monoclonal antibodies, hybridomas, and diploid cells have been described in detail, particularly with reference to specific embodiments included by way of the examples. It will be understood that the products and techniques of the present invention are of far-reaching significance in the field of cancer detection and treatment. They include a wide range of monoclonal antibodies, each specific for determinants found on an individual strain of tumor forming cancer, as the technique disclosed herein can be used to generate antibodies for every such case. It will be further understood that many variations and modifications of the techniques disclosed herein are available to those of ordinary skill in the relevant art and that such variations and modifications are contemplated as being within the scope of the invention.

The embodiments provided to illustrate this invention relate to carcinoma tumors, particularly well-differentiated colorectal adenocarcinomas. Clearly, however, the invention pertains to all carcinomas, such as lung, breast, and other malignancies in areas which arise from the same type of embryonic tissue. Moreover, the procedures described can be adjusted, if necessary, by one skilled in the art to be used to apply this invention to other types of cancer.

The cells line producing the IgG-3 human monoclonal antibody 88BV59 were deposited with the American Type Culture Collection, 12301 Parklawn Drive, Rockville, Md. 20852, U.S.A., on Dec. 13th, 1990, and Jan. 31, 1994. The cell lines deposited are identified as follows:

| Identification | Accession Number |
| --- | --- |
| Human B-Cell Derived Cell Line, CO88BV59-1 (deposited December 13, 1990) | CRL 10624 |
| Human B-Cell Derived Cell Line, CO88BV59H21-2 (deposited January 31, 1994) | CRL 11538 |
| Human B-Cell Derived Cell Line, CO88BV59H21-2V67-66 (deposited January 31, 1994) | CRL 11539 |

TABLE 1

CRITERIA FOR SUCCESSFUL VACCINES FOR ACTIVE SPECIFIC IMMUNOTHERAPY

Adjuvant (a) BCG (Phipps, Tice, Connaught); Lyophilized, frozen (dose-dependence > $10^6$ ($10^7$–$10^8$))
(b) *C. parvum* (Wellcome Labs) (dose-dependence > 7 μg (70 μg–700 μg)

Tumor Cells (a) Enzymatic dissociation
   (1) Collagenase type I (1.5–2.0 U/ml HESS)
   (2) DNAase (450 D.U./ml HBSS)
   (3) 37° C. with stirring
(b) Cryopreservation
   (1) Controlled-rate freezing (–1° C./min) (7.5% DMSO, 5% HSA, HBSS)
   (2) Viability 80%
(c) X-irradiation
   (1) Rendered non-tumorigenic at 12,000–20,000 R.

Components and Administration[1]

(a) Ratio of adjuvant to tumor cells - 10:1–1:1 (optimum)
(b) $10^7$ tumor cells (optimum)
(c) 2–3 i.d. vaccinations at weekly intervals. Third

TABLE 1-continued

CRITERIA FOR SUCCESSFUL VACCINES FOR ACTIVE SPECIFIC IMMUNOTHERAPY vaccination contains tumor cells only.

[1]Isoniazid chemoprophylaxis of BCG infection optional.
BCG - Bacillus Calmette Guerin
HBSS - Hanks' Balanced saline solution
DMSO - Dimethylsulfoxide
HSA - Human serum albumin
R - Rads
PBS - Phosphate buffered saline
EDTA - Ethylenediaminetetraacetic acid

TABLE 2

REACTIVITY OF HUMAN MONOCLONAL ANTIBODY 88BV59
Indirect Immunofluorescence with Acetone-filed Tumor Cells[a]

| Cell Line | Tumor Type | Fluorescence Intensity[a] |
| --- | --- | --- |
| Ht-29 | Colon Carcinoma | 3+ |
| SKCO-1[c] | Colon Carcinoma | 3+ |
| LS174 | Colon Carcinoma | 4+ |
| WiDr | Colon Carcinoma | N.T.[e] |
| HCT-8 | Colon Carcinoma | − |
| Bt-20[b] | Breast Carcinoma | 3+ |
| EP[b] | Breast Carcinoma | 2+ |
| MCF-7 | Breast Carcinoma | 4+ |
| SKBR-III | Breast Carcinoma | − |
| CaLu-1[c] | Lung Adenocarcinoma | 4+ |
| A2780 | Ovarian Carcinoma | − |
| Ovcar3[c] | Ovarian Carcinoma | 4+(30%)[d] |
| WI-38 | Normal Fibroblasts | − | a) Florescence Intensity: 4+ strong, 3+ moderate, 2+ weak to moderate, 1+ weak, − negative. Concentration of 88BV59-1 was 10 μg/ml. Staining with a control human IgG at 10 ηg/ml was negative on all cells.
b) Staining preferentially on cells in mitosis.
c) Staining shows a filamentous cytoskeletal staining pattern.
d) Percentage of cells showing the indicated fluorescence intensity was 100% unless otherwise noted.
e) NT = not tested.

TABLE 3

REACTIVITY OF 88BV59 WITH VARIOUS TUMOR TYPES

| Tumor Type | Number of Reactive Tissues | Total Number of Tissues Tested | Percentage |
| --- | --- | --- | --- |
| Colon | 17 | 23 | 74 |
| Breast | 19 | 19 | 100 |
| Ovarian | 13 | 17 | 76 |
| Pancreatic | 3 | 9 | 33 |
| Lung | 3 | 4 | 75 |
| Prostate | 4 | 6 | 67 |

We claim:

1. A transformed human lymphocyte cell line designated 88BV59-1, ATCC accession number CRL 10624, and subclones thereof.

2. A transformed human lymphocyte cell line designated 88BV59H21-2, ATCC accession number CRL 11538, and subclones thereof.

3. A transformed human lymphocyte cell line designated 88BV59H21-2V67-66, ATCC accession number CRL 11539, and subclones thereof.

4. A human monoclonal antibody 88BV59, produced by a transformed human lymphocyte cell line selected from the group consisting of ATCC CRL 10624, ATCC CRL 11538, ATCC CRL 11539 and a subclone thereof, or an antigen binding fragment of human monoclonal antibody 88BV59.

5. A method for identifying tumor cells, comprising:
   (a) contacting human tissue with a human monoclonal antibody or antigen binding fragment according to claim 4, in an amount that is sufficient to be detectable; and
   (b) detecting the antibody or antigen binding fragment bound to the human tissue, whereby tumor cells will be identified, the method for detecting the antibody or antigen binding fragment being selected from the group consisting of labeling the antibody or antigen binding fragment before contacting the human tissue and detecting the label, and contacting the human tissue with a labeled moiety having binding affinity for the human antibody or antigen binding fragment and detecting the labeled moiety.

6. The method of claim 5, wherein the human monoclonal antibody or antigen binding fragment is labeled with a radiolabel.

7. The method of claim 6, wherein the antibody or antigen binding fragment bound to tumor cells is detected using a scanning device.

8. The method of claim 7, wherein the method is conducted in vivo.

9. The method of claim 8, wherein the method is conducted in vitro.

10. An antibody comprising the variable light chain and the variable heavy chain of a human monoclonal antibody of claim 4.

11. The human monoclonal antibody according to claim 4, wherein the $CH_2$ region is deleted.

* * * * *